(12) United States Patent
Schneider et al.

(10) Patent No.: US 8,002,944 B2
(45) Date of Patent: *Aug. 23, 2011

(54) METHOD OF PLACING A MATERIAL TRANSVERSELY ON A MOVING WEB

(75) Inventors: Uwe Schneider, Mason, OH (US); Christoph Schmitz, Euskirchen (DE)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/698,208

(22) Filed: Feb. 2, 2010

(65) Prior Publication Data

US 2010/0132872 A1    Jun. 3, 2010

Related U.S. Application Data

(60) Continuation of application No. 11/707,306, filed on Feb. 16, 2007, now Pat. No. 7,666,271, which is a division of application No. 10/779,338, filed on Feb. 13, 2004, now Pat. No. 7,201,822.

(51) Int. Cl.
*C09J 5/00* (2006.01)
(52) U.S. Cl. ...... 156/324; 226/8; 226/196.1; 427/207.1; 427/209
(58) Field of Classification Search .................. 156/324; 226/1, 2, 8, 196.1; 427/207.1, 208, 209, 427/425

See application file for complete search history.

(56) References Cited

U.S. PATENT DOCUMENTS

| 4,642,151 A | | 2/1987 | Coenen |
| 4,788,846 A | * | 12/1988 | Morita et al. .................... 72/160 |
| 4,987,940 A | | 1/1991 | Straub et al. |
| 5,127,981 A | | 7/1992 | Straub et al. |
| 5,693,165 A | | 12/1997 | Schmitz |
| 6,349,867 B1 | | 2/2002 | Fernfors |
| 6,443,935 B1 | | 9/2002 | Gustafsson et al. |
| 6,595,465 B2 | | 7/2003 | Lamothe |

FOREIGN PATENT DOCUMENTS

| EP | 0 284 652 A2 | 10/1988 |
| EP | 0 364 087 A1 | 4/1990 |

OTHER PUBLICATIONS

PCT Search Report, mailed Jul. 6, 2005, 3 pages.

* cited by examiner

*Primary Examiner* — John L Goff, II
(74) *Attorney, Agent, or Firm* — Charles R. Matson (57) ABSTRACT

Disclosed herein is a method by which a material may be placed onto a moving web in a transverse orientation. At least two assemblies, which carry either a first and a second web or a single web, periodically overlap each other in an alternating fashion such that a material may be placed upon their respective carried webs in a transverse manner. The first and second assemblies translate in a direction of web movement in order to modify the velocity of the web carried upon the assembly. Thus, with the velocities of the assemblies capable of being varied, the material may be placed in a transverse manner upon the moving web along with various other orientations.

5 Claims, 10 Drawing Sheets

METHOD OF PLACING A MATERIAL TRANSVERSELY ON A MOVING WEB

CROSS REFERENCE TO RELATED APPLICATION

This application is a continuation of U.S. application Ser. No. 11/707,306, filed Feb. 16, 2007, now U.S. Pat. No. 7,666,271 which is a divisional of U.S. application Ser. No. 10/779,338, filed Feb. 13, 2004, now U.S. Pat. No. 7,201,822, which are all incorporated herein by reference.

FIELD OF THE INVENTION

The present invention relates to a process by which a material can be placed onto a moving web and more particularly to a process by which a material can be placed onto a moving web across at least a portion of the transverse width of the web.

BACKGROUND OF THE INVENTION

There are many processes which allow for the application of material across the transverse width of a web. However, many of these processes accomplish this feat at the cost of affecting the speed of the entire web.

An example of modifying the speed of only a portion of the web as opposed to modifying the speed of the entire web is shown in U.S. Pat. No. 5,693,165 issued to Schmitz. The Schmitz reference teaches that a pair of translatable transport rollers may be used in conjunction with a pair of stationary guide rollers to affect a velocity change in a portion of the web. The transport rollers are mounted on a sled which is periodically translated along a frame. Because the web is looped around the translatable transport rollers, as the sled translates along the frame in the direction of web feed, the web portion between the two translatable transport rollers has a velocity which is less than that of the overall web velocity. Therefore, a process could be implemented wherein a material is placed onto the portion of the web having a reduced velocity.

European Patent Application EP-A-0 364 087 discloses an applicator device for applying layers of material generally transversely across an elongated web. The elongated web moves continuously through the device in a web feed direction at a predetermined web speed. The device comprises two transport members which each turn the web 90 degrees in the plane of the web. The web portion between the two transport members is of constant length and extends perpendicular to the upstream portion of the web. The transport members are mounted on a sled which translates in the web feed direction and the reverse web feed direction. When the sled translates in the web feed direction at a speed which equals the web speed, the web portion between the transport members is stationary relative to the frame. A rotating applicator wheel having a tangential speed, which equals the linear speed of the air bars, can contact the web portion to attach a layer of material. When the frame is translated in the reverse web feed direction, the web portion is accelerated past the transport members to the web's downstream side.

From European Patent application EP-A-0 284 652 it is known to supply tensioned elastic ribbons transversely to a continuously moving web at a high speed. A number of applicator heads are mounted on a rotatable vertical shaft with each applicator head being connected to a radial arm. Upon rotation of the shaft, the arms pass over the moving web. At the position when a radial arm extends perpendicular to the web and has a tangential velocity equal to the linear web speed, a pre-stretched elastic is fed from the applicator head. A rotating anvil, which has a circumferential velocity equal to the linear web speed to minimize the shearing forces, contacts the applicator head upon attachment of the elastic.

Because the above apparatus has multiple arms, it can attach transverse parts to the moving web at a high speed and exert a low tension on the web with the web speed remaining constant. But, the application of complex parts in a transverse orientation to the web may require momentarily stopping the web at the position of the applicator device. In this instance, the above apparatus is less suitable.

It is an object of the present invention to provide a method by which a material may be applied to a moving web transversely without affecting the overall processing speed of the web regardless of the complexity of the material to be applied to the web.

SUMMARY OF THE INVENTION

The present invention pertains to a method of placing a material on a plurality of webs. The method comprises the steps of providing a first path comprising a first upstream zone, a first downstream zone, and a first intermediate zone which is disposed between the first upstream zone and the first downstream zone. Also, a second path is provided comprising a second upstream zone, a second downstream zone, and a second intermediate zone which is disposed between the second upstream zone and the second downstream zone. In addition, the first intermediate zone comprises a first assembly, and the second intermediate zone comprises a second assembly.

A first web having a transverse width and a longitudinal centerline is provided in the first upstream zone of the first path such that the first web is moving at a first web velocity in the positive x direction. The first assembly is provided for diverting the first web from the first upstream zone to the first intermediate zone of the first path. The first assembly also diverts the first web from the first intermediate zone to the first downstream zone of the first path.

Similarly, a second web having a transverse width and a longitudinal centerline is provided in the second upstream zone of the second path such that the second web is moving at a second web velocity in the positive x direction. The second assembly is provided for diverting the second web from the second upstream zone to the second intermediate zone of the second path and for diverting the second web from the second intermediate zone to the second downstream zone of the second path.

The method further comprises the step of periodically overlapping the first and second assemblies in an alternating fashion. This is accomplished by translating the first assembly and the second assembly in a positive x direction in a first plane and a negative x direction in a second plane. So, when the first assembly translates in the positive x direction, the first web in the first intermediate zone has a velocity, with respect to the first assembly, which is less than the first web velocity. Similarly, when the second assembly translates in the positive x direction, the second web in the second intermediate zone has a velocity, with respect to the second assembly, which is less than the second web velocity.

As the first and second assemblies are being overlapped, a material is being alternately applied across at least a portion of the transverse width of the first web in the first intermediate zone and across at least a portion of the transverse width of the second web in the second intermediate zone. As a result of the alternate application of the material to the first web and the second web, the application of the material is continuous.

Alternatively, the claimed invention may be performed on a single web rather than the previously stated plurality of webs. In this instance, the method includes the step of providing a single web to a first upstream zone such that the single web is moving at a first upstream zone velocity. Also, a first assembly is provided for diverting the single web from a first upstream zone to a first intermediate zone. The first assembly also diverts the single web in the first intermediate zone to a first downstream zone. From the first downstream zone, the single web is transported into a second upstream zone such that the single web is moving at a second upstream zone velocity in the positive x direction. In addition, a second assembly is provided for diverting the single web from the second upstream zone to a second intermediate zone. The second assembly also diverts the single web from the second intermediate zone to a second downstream zone.

This method further comprises the step of periodically overlapping the first and second assemblies in an alternating fashion. This is accomplished by translating the first assembly and the second assembly in a positive x direction in a first plane and a negative x direction in a second plane. So, when the first assembly translates in the positive x direction, the single web in the first intermediate zone has a velocity, with respect to the first assembly, which is less than the first upstream zone velocity. Similarly, when the second assembly translates in the positive x direction, the single web in the second intermediate zone has a velocity, with respect to the second assembly, which is less than the second upstream zone velocity. As the assemblies periodically overlap in an alternating fashion, a material is continuously applied across at least a portion of the transverse width of the single web in the first intermediate zone and the transverse width of the single web in the second intermediate zone.

DETAILED DESCRIPTION OF THE INVENTION

Definitions

As used herein, the following terms have the following meanings:

The term "continuous" when used to refer to a process, means that the process, when in operation, can run without stopping; however, the process can be stopped. When used to refer to a web, the term "continuous" means that the web subjected to the process is sufficiently long such that the first and second assemblies, later defined herein, can each perform at least two complete cycles.

The term "web," as used herein, implies a continuous web and may comprise non-wovens, wovens, films, tissues, laminate structures, or any combination thereof.

The term "cycle" refers an interval of time characterized by the occurrence of a sequence of events. In this instance, the cycle for an assembly begins when its web receives a material on its leading edge. Subsequently, the web via its assembly moves in such a manner so that the web can receive the material again. The end of the cycle for the assembly occurs at a time immediately prior to the material contacting the web on its leading edge.

As used herein the term "machine direction," designated MD, is the direction parallel to the flow of the web through the equipment.

As used herein the term "cross machine direction," designated CD, is the direction that is substantially perpendicular to the machine direction.

As used herein the term "transverse width" is the width of the web in the CD direction.

As used herein, the x-axis is parallel to the longitudinal centerline of the web(s) of the first and second upstream and downstream zones.

As used herein, the y-axis is perpendicular to the x-axis and the longitudinal centerline of the web(s) of the first and second upstream and downstream zones.

As used herein, the z-axis is perpendicular to the x-axis, the y-axis, and the top surface of the web.

Description

Figure 1:
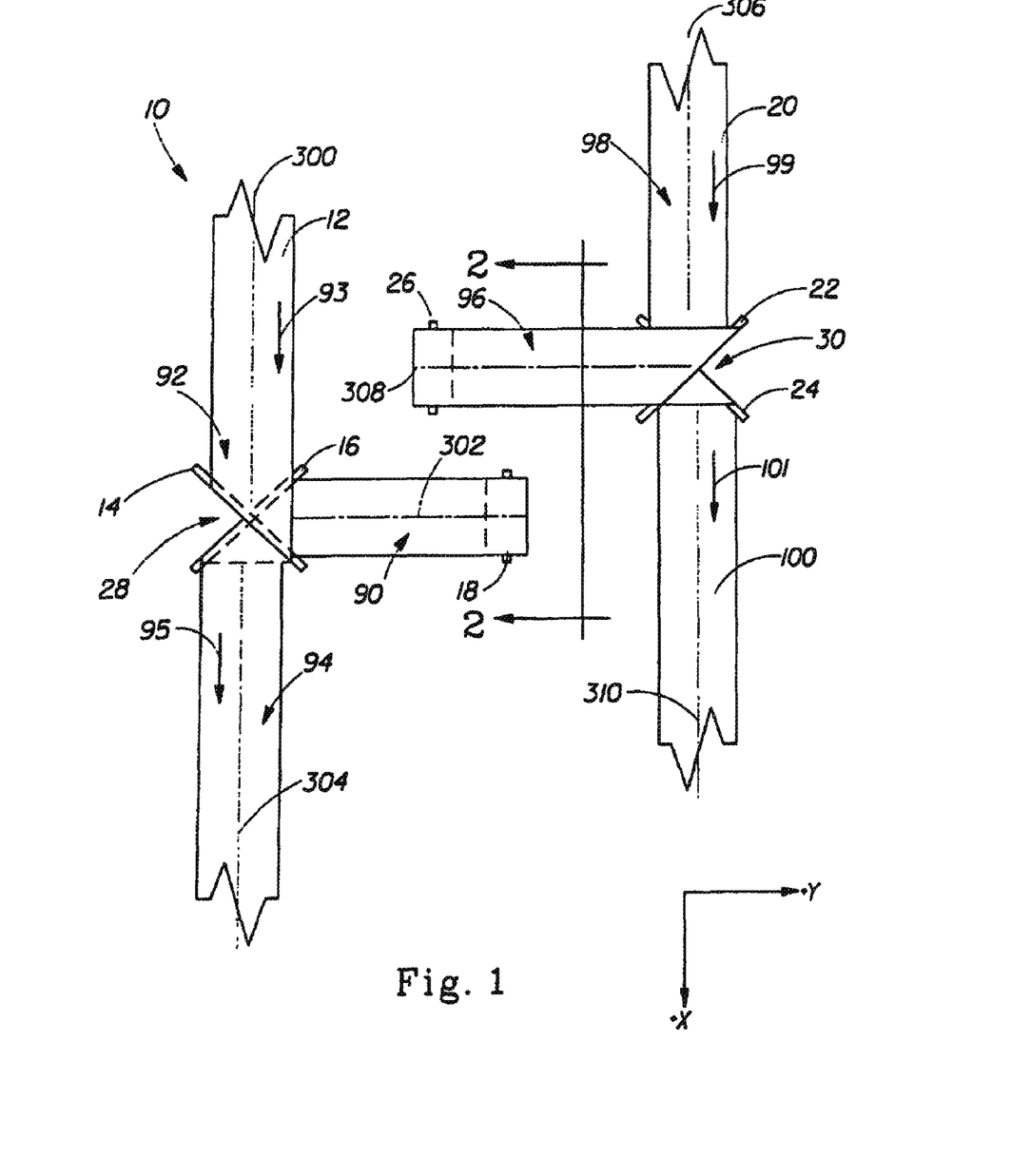
FIG. 1 is a plan view of an apparatus that can carry out the present invention.

FIG. 1 shows an example of an apparatus 10 that can carry out the present invention. A first web 12 is provided in a first upstream zone 92 moving in the positive x direction 93 at a first web velocity. A first assembly 28 is provided to divert the first web 12 from the first upstream zone 92 to a first intermediate zone 90. The first web 12 is diverted by a first turnbar 14 such that the first web extends in the positive y direction toward a second assembly 30. The first web 12 is turned, such that the longitudinal centerline 302 of the first web 12 in the first intermediate zone 90 is perpendicular to the longitudinal centerline 300 of the first web 12 in the first upstream zone 92.

The first web 12 is fed to a first idler 18 such that the first web 12 in the first intermediate zone 90 is inverted. The first web 12 is inverted such that the first web 12 extends in the negative y direction away from the second assembly 30. The first web 12 is then fed to a second turnbar 16 where the first web 12 is diverted from the first intermediate zone 90 to a first downstream zone 94. The first web 12 is turned such that the longitudinal centerline 304 of the first web 12 in the first downstream zone 94 is parallel to the x-axis and moves in the positive x direction 95.

Similarly, a second web 20 is provided in a second upstream zone 98 moving in the positive x direction 99 at a second web velocity. The second assembly 30 is provided to divert the second web 20 from the second upstream zone 98 to a second intermediate zone 96. The second web 20 is diverted by a third turnbar 22 such that the second web extends in the negative y direction toward the first assembly 28. The second web 20 is turned, such that the longitudinal centerline 308 of the second web 20 in the second intermediate zone 96 is perpendicular to the longitudinal centerline 306 of the second web 20 in the second upstream zone 98.

The second web 20 is fed to a second idler 26 such that the second web 20 in the second intermediate zone 96 is inverted. The second web 20 is inverted such that the second web 20 extends in the positive y direction away from the first assembly 28. The second web 20 is then fed to a fourth turnbar 24 where the second web 20 is diverted from the second intermediate zone 96 to a second downstream zone 100. The second web 20 is turned such that the longitudinal centerline 310 of the second web 20 in the second downstream zone 100 is parallel to the x-axis and moves in the positive x direction 101.

As shown in FIGS. 2-5, a material applicator 32 is provided for placing a material 34 onto a first web 12 and a second web 20. The material 34 can be a polymer as exampled by an adhesive or an elastomeric material. The material 34 can also be a thermoplastic or any non-woven fiber. Also, the material 34 may comprise a web from which discrete parts are formed, as discussed with regard to FIG. 15. Moreover, the material applicator 32 may apply the material 34 via an extrusion process, a spraying process or a joining process or any combination thereof.

Figure 2:
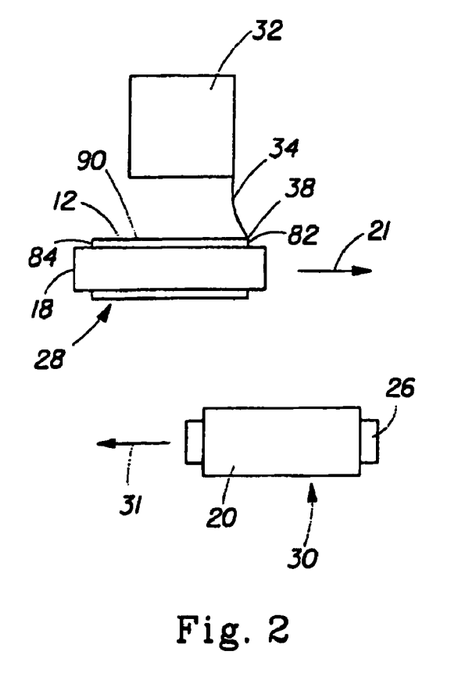
FIGS. 2-5 show a cross sectional view of the apparatus shown in FIG. 1 illustrating an example of the motion of the two assemblies relative to one another.

In FIG. 2, a distal end 38 of the material 34 is shown in contact with the leading edge 82 of the first web 12 which marks the beginning of the first assembly's cycle. The first web 12 in the first intermediate zone 90 continues to receive the material 34 as the first assembly translates in the positive x direction along a first plane 21. Because the first assembly 28 translates in the positive x direction, the first web 12 in the first intermediate zone 90 has a velocity, with respect to the first assembly 28, which is lower than the first web velocity. In contrast, the second assembly 30 translates in the negative x direction along a second plane 31 such that the second web 20 in the second intermediate zone 96 has a velocity, with respect to the second assembly 30, which is greater than the second web velocity.

Figure 3:
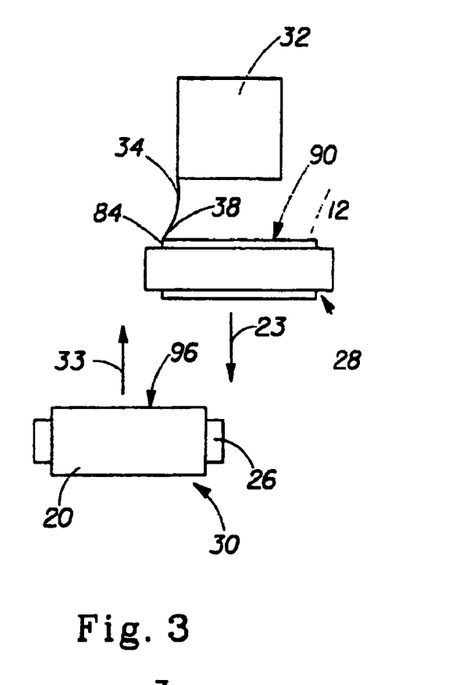

As shown in FIG. 3, the distal end 38 of the material 34 is in contact with the trailing edge 84 of the first web 12. After the material 34 has been applied across the transverse width of the first web 12 in the first intermediate zone 90, the first assembly 28 moves along the z-axis in the negative z direction 23. The second assembly 28 moves along the z-axis in the positive z direction 33 such that the second web 20 in the second intermediate zone 96 can receive the material 34 across its transverse width.

Figure 4:
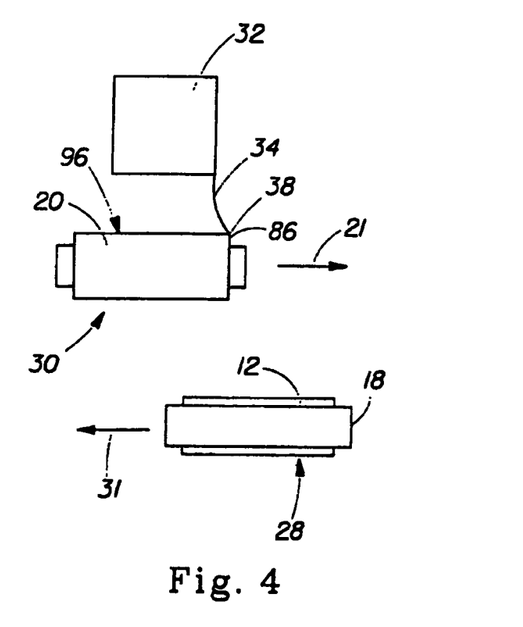

As shown in FIG. 4, the distal end 38 of the material 34 is in contact with the leading edge 86 of the second web 20 in the second intermediate zone 96 which marks the beginning of the second assembly's cycle. The second web 20 in the second intermediate zone 96 continues to receive the material 34 as the second assembly 30 translates in the positive x direction along the first plane 21. Because the second assembly 30 translates in the positive x direction, the second web 20 in the second intermediate zone 96 has a velocity, with respect to the second assembly 30, which is lower than the second web velocity. Contemporaneously, the first assembly 28 translates in the negative x direction along the second plane 31 such that the first web 12 in the first intermediate zone 90 has a velocity, with respect to the first assembly 28, which is greater than the first web velocity.

Figure 5:
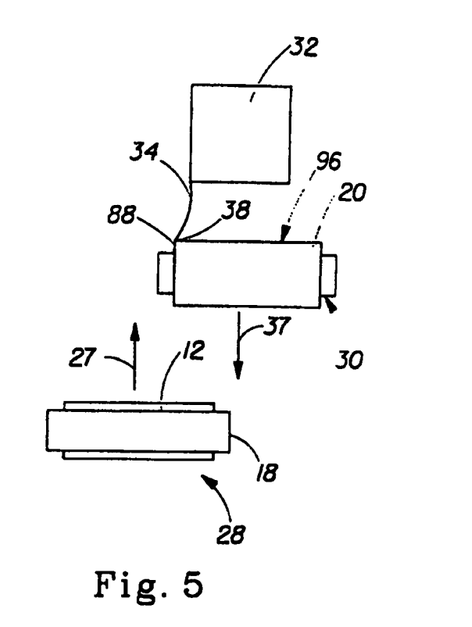

As shown in FIG. 5, the distal end 38 of the material 34 is in contact with the trailing edge 88 of the second web 20. After the material 34 has been applied across the transverse width of the second web 20 in the second intermediate zone 96, the second assembly 30 moves in the negative z direction 37. The first assembly 28 moves along the z-axis in the positive z direction 27 such that the first web 12 in the first intermediate zone 90 can receive the material 34 across its transverse width.

The end of the cycle for the first assembly 28 corresponds to the moment immediately before the distal end 38 of the material 34 contacts the leading edge 82 of the first web 12. Similarly, the end of the cycle for the second assembly 30 is the moment immediately before the distal end 38 of the material 34 contacts the leading edge 86 of the second web 20.

Although not shown in FIG. 3, when the distal end 38 of the material 34 contacts the trailing edge 84 of the first web 12, the second assembly 30 is positioned immediately behind the first assembly 28 such that the risk of losing material between the first assembly 28 and the second assembly 30 is minimized. Similarly, although not shown in FIG. 5, when the distal end 38 of the material 34 contact the trailing edge 88 of the second web 20, the first assembly 28 is positioned immediately behind the second assembly 30.

In the preceding figures, i.e. 2-5, the movement of both the first assembly 28 and the second assembly 30 were shown as orthogonal to either the x-axis or z-axis merely as examples of the movements of the assemblies. However, the assemblies are not constrained to move solely in directions which are orthogonal to an axis described herein. Moreover, the movements of the assemblies are not constrained to move solely in a linear fashion. For instance, the assembly movement may comprise a curvilinear path.

Figure 6:
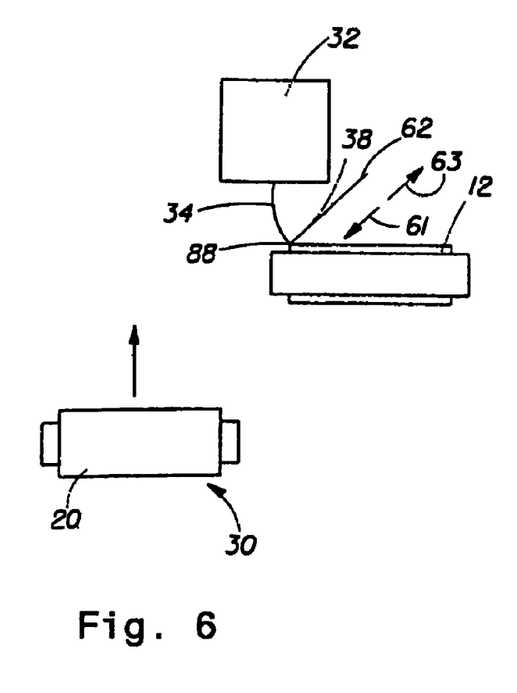
FIGS. 6-7 show a cross sectional view of the apparatus shown in FIG. 1 illustrating an example of the assembly motion that can perform an optional step in the claimed invention.
Figure 7:
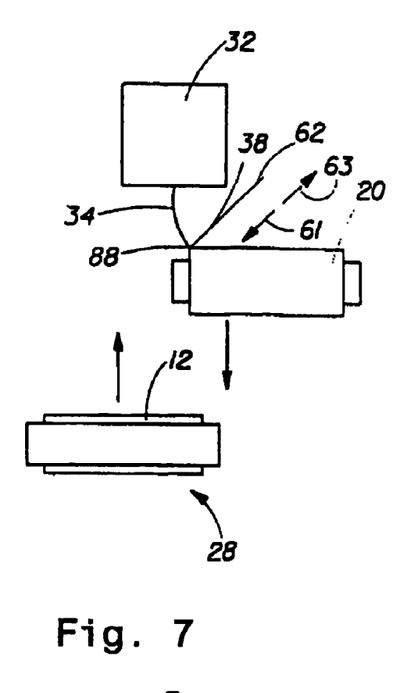

A separating step may be included in the present invention (see FIG. 6). A separator 62 may be employed such that the material 34 is separated from the trailing edge 84 of the first web 12. When the distal end 38 of the material 34 contacts the trailing edge 84 of the first web 12, the separator 62 moves along a path 61. The separator 62 severs the distal end 38 of the material 34 from the trailing edge 84 of the first web 12. The separator 62 then moves along a path 63 such that the separator 62 does not disturb the movement of the first assembly 28 or second assembly 30. The separator 62 operates in a similar manner when severing the distal end 38 of the material 34 from the trailing edge 88 of the second web 20 (See FIG. 7).

Because there are so many possibilities with regard to either the material 34 or the process utilized by the material applicator 32 to apply the material 34, the step of separation may be accomplished in many different ways. The separator 62 can be a knife-edge which severs the distal end 38 of the material 34 from the trailing edge 84 of the first web 12 or the trailing edge 88 of the second web 20. Moreover, if the material 34 comprises discrete parts, the separator may comprise a knife roll and an anvil roll (see discussion of FIG. 15). The separator 62 may also comprise a hot air knife, a hot wire, a water jet, a laser, or any means of separation that is well known in the art.

Alternatively, the step of separation of the material 34 from the trailing edge 84 of the first web 12 or the trailing edge 88 of the second web 20 can be accomplished by changing the velocity profile of the first assembly 28 or the velocity profile of the second assembly 30. For example, when the distal end 38 of the material 34 is in contact with the trailing edge 84 of the first web 12, the first assembly 28 accelerates to a higher velocity in the positive x direction than the velocity of the first assembly 28 when the first web 12 is receiving the material 34. This acceleration to a higher velocity induces the material 34 to break, thereby accomplishing the step of separation. Similarly, when the distal end 38 of the material 34 contacts the trailing edge 88 of the second web 20, the separation of the material 34 from the trailing edge 88 of the second web 20 can be accomplished by accelerating the second assembly 30.

Alternatively, the step of separation may be accomplished via a timed process. For instance, if the material is an adhesive to be sprayed onto the first web 12, the material applicator 32 ceases the process when the trailing edge 84 of the first web 12 is no longer underneath the material applicator 32. In this instance, the material applicator 32 ceases spraying the adhesive in between the trailing edge 84 of the first web 12 and the leading edge 86 of the second web 20, and the material applicator 32 begins spraying once the leading edge 86 of the second web 20 is underneath the material applicator 32. Similarly, the material applicator 32 ceases spraying between the trailing edge 88 of the second web 20 and the leading edge 82 of the first web 12.

Figure 8:
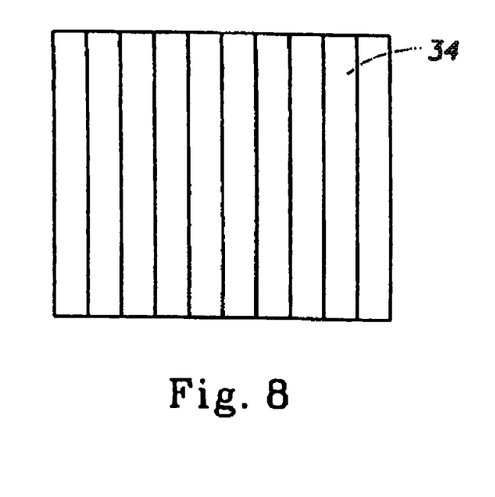
FIG. 8 is a view of a portion of web material showing the uniform application of material onto the portion of the web.

FIGS. 8, 9, 10, and 11, are examples of the orientation of the material 34 on either the first, second, or single web. In FIG. 8, the material 34 is shown applied in a uniform manner to the web material perpendicular to the y-axis. As an example of how to accomplish this, the first assembly translates in the positive x direction at the first web velocity such that the first web in the first intermediate zone is stationary with respect to the first assembly. Because the first web in the first intermediate zone is stationary with respect to the first assembly, the material is applied across the transverse width of the first web in the first intermediate zone such that the material is perpendicular to the longitudinal centerline of the first web.

Figure 8A:
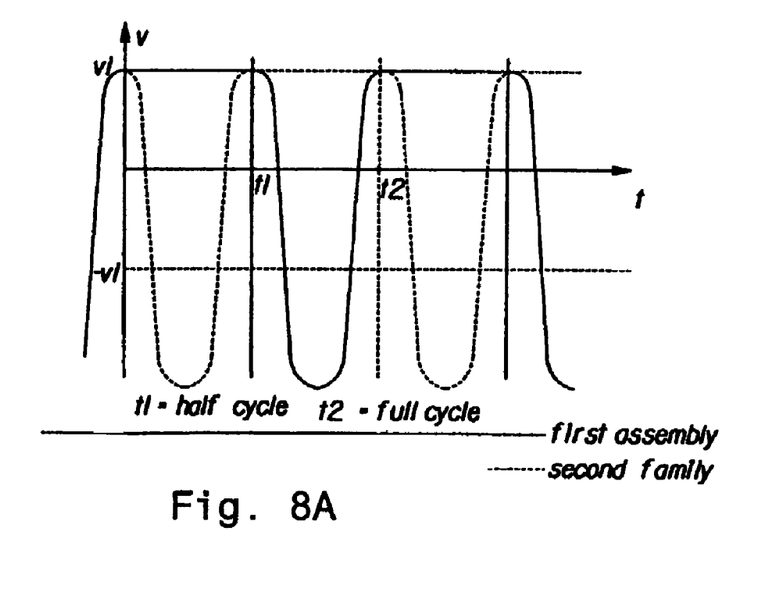
FIG. 8A is a graph of an example of the velocity profiles of the first and second assembly.

FIG. 8A provides examples of the velocity profiles of the assemblies for accomplishing the material orientation as shown in FIG. 8. As shown, time, denoted as "t", t equal to zero, the first web in the first intermediate zone begins to receive the material. While receiving the material, the velocity of the first assembly in the positive x direction, denoted v1, is equal to the first web velocity. At time t equal to t1 (t1 representing the completion of 50% of the cycle for the first assembly); the transverse width of the first web has received the material. The first assembly subsequently completes the remainder of its cycle and gets back into a position such that the first web may receive the material again. Because 50% of the first assembly's cycle is spent receiving material across the transverse width of the first web, during the remaining 50% of the cycle, the amount of web which travels through the first intermediate zone is equal to the transverse width of the first web. Therefore, the material applicator provides the material to the first web in the first intermediate zone on a portion of the first web having a length which is two times the transverse width of the first web.

The velocity profile of the second assembly is similar to that of the first assembly; however, the second web in the second intermediate zone begins to receive the material at t equal to t2. Similarly, at t equal to t3 (t3 representing the completion of 50% of the cycle for the second assembly) the transverse width of the second web has received the material.

Figure 9:
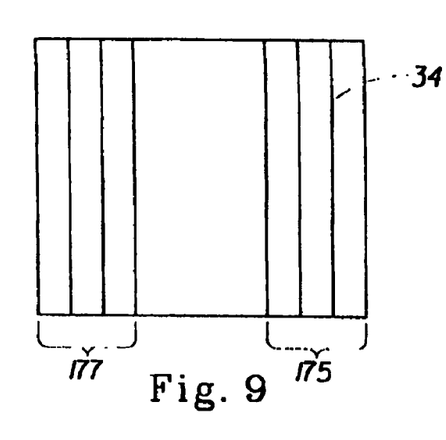
FIG. 9 is a view of a portion of web material showing a variant of uniform application of the material onto the portion of the web.

In FIG. 9, the material 34 is shown applied to the web in the first intermediate zone of the first assembly in two separate material applications 175 and 177. During the first application 175 of the material 34 to the first web, the velocity of the first assembly while translating in the positive x direction is equal to the first web velocity. The translation of the first assembly in the positive x direction at the first web velocity causes the first web in the first intermediate zone to be stationary with respect to the first assembly. The first web in the first intermediate zone receives the material 34 across its transverse width for 50% of the first assembly's cycle. The remaining 50% of the cycle, the first assembly alternates positions with the second assembly and moves such that the first web can receive the material 34 during the second application 177. Similar to the first application 175, during the second application 177 of material 34, the first assembly translates in the positive x direction at a velocity which equals the first web speed.

In this instance, however, the gap between the first application 175 and the second application 177 occurs because during the first application 175 the material applicator does not provide material 34 to a portion of the first web having a length which is two times the transverse width of the first web. Instead, the material applicator applies the material 34 to a length of the first web which is less than two times the transverse width of the first web. Thus, before the second application 177 of material 34 begins, a portion of the first web passes through the first intermediate zone without receiving the material 34.

Figure 10:
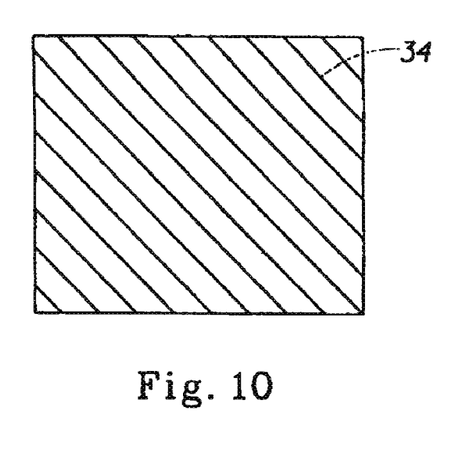
FIG. 10 is a view of a portion of web material showing the angled application of the material onto the portion of the web.

FIG. 10, shows the orientation of the material 34 on the web when the velocity of the first assembly in the positive x direction is less than the first web velocity. If this is in fact the case, then the first web in the first intermediate zone has a positive velocity with respect to the first assembly. Because the first web in the first intermediate zone has a positive velocity with respect to the first assembly, the first web translates in the positive y direction thereby yielding a pattern similar to that shown in FIG. 10.

Figure 11:
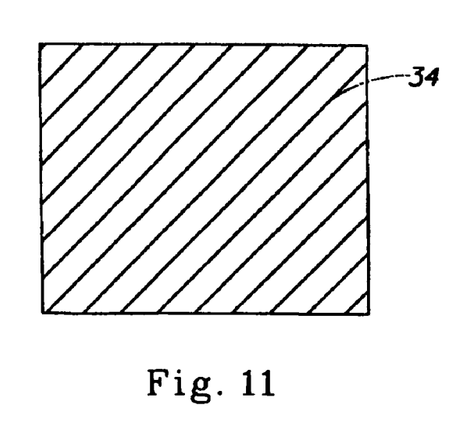
FIG. 11 is a view of a portion of web material showing the angled application of the material onto the portion of the web.

FIG. 11, shows the orientation of the material 34 on the web when the velocity of the first assembly in the positive x direction is greater than the first web velocity. If this is in fact the case, then the first web in the first intermediate zone, with respect to the first assembly, has a negative velocity with respect to the assembly. This causes the first web in the first intermediate zone to travel in the negative y direction with respect to the first assembly.

Note that in both FIGS. 10 and 11, reference was made only to the first web. The same holds true for the second web; however, a positive second web velocity with respect to the second assembly, i.e. the second assembly is translating at a higher velocity than the velocity of the second web, causes the second web in the second intermediate zone to translate in the positive y direction. Therefore, a pattern similar to that shown in FIG. 10 would occur. In contrast, a negative second web velocity with respect to the second assembly (the second assembly translates at a lower velocity than the velocity of the second web) causes the second web in the second intermediate zone to translate in the negative y direction with respect to the assembly. Therefore, a pattern similar to that shown in FIG. 11 occurs.

Figure 12:
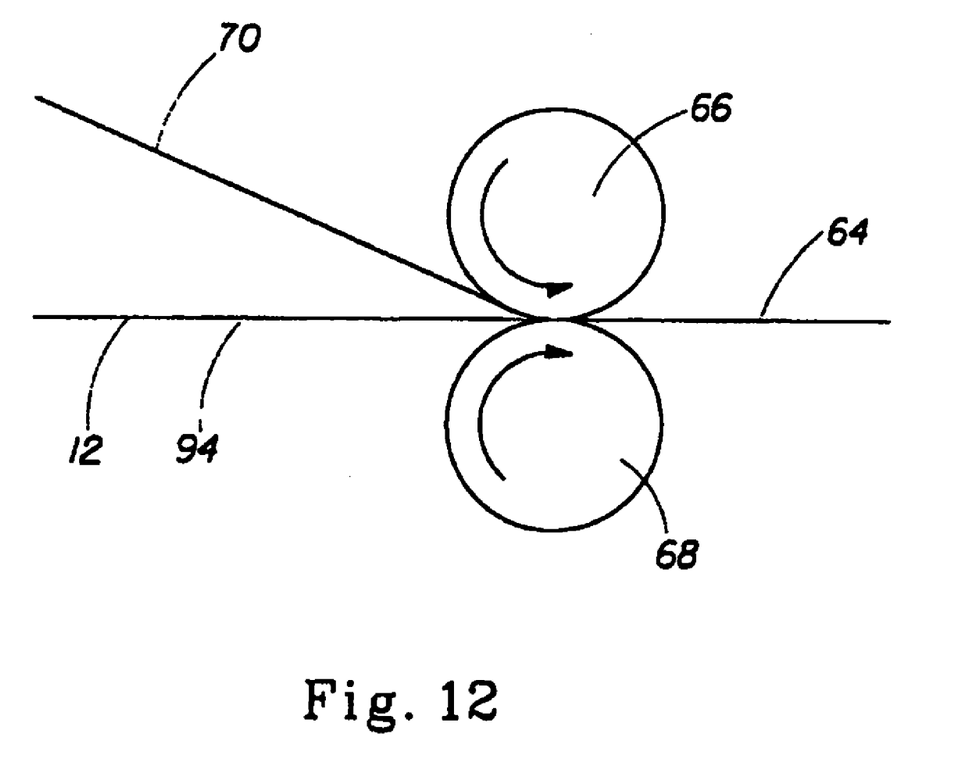
FIG. 12 is a cross sectional view of an apparatus implementing an optional step in the claimed invention.

Once the material 34 has been applied to the first web 12 or the second web, then a laminate structure 64 may be formed by joining the first web 12 or second web with a third web 70 or fourth web, respectively. FIG. 12 shows an example of how the laminate structure can be formed. The first web 12 in the first downstream zone 94 proceeds into a nip roll at which point the first web 12 is combined with the third web 70. The combination or nipping takes place between roll A 66 and roll B 68. The combination of the first web 12 and the third web 70 produces a laminate structure 64 on the downstream side of the nipping step. Similarly, although not shown in this figure, the second web could be combined with a fourth web in a similar manner. The discussion pertaining to the addition of the joining step for a single web application occurs in the section pertaining to FIG. 14.

The orientation of the web face prior to the joining step may be of concern. For example, if the material were an elastic, over which a third web 70 or fourth web were to be placed, then the web going over a turnbar needs to be positioned such that the elastic were facing upward on the downstream side of the turnbar.

Figure 13:
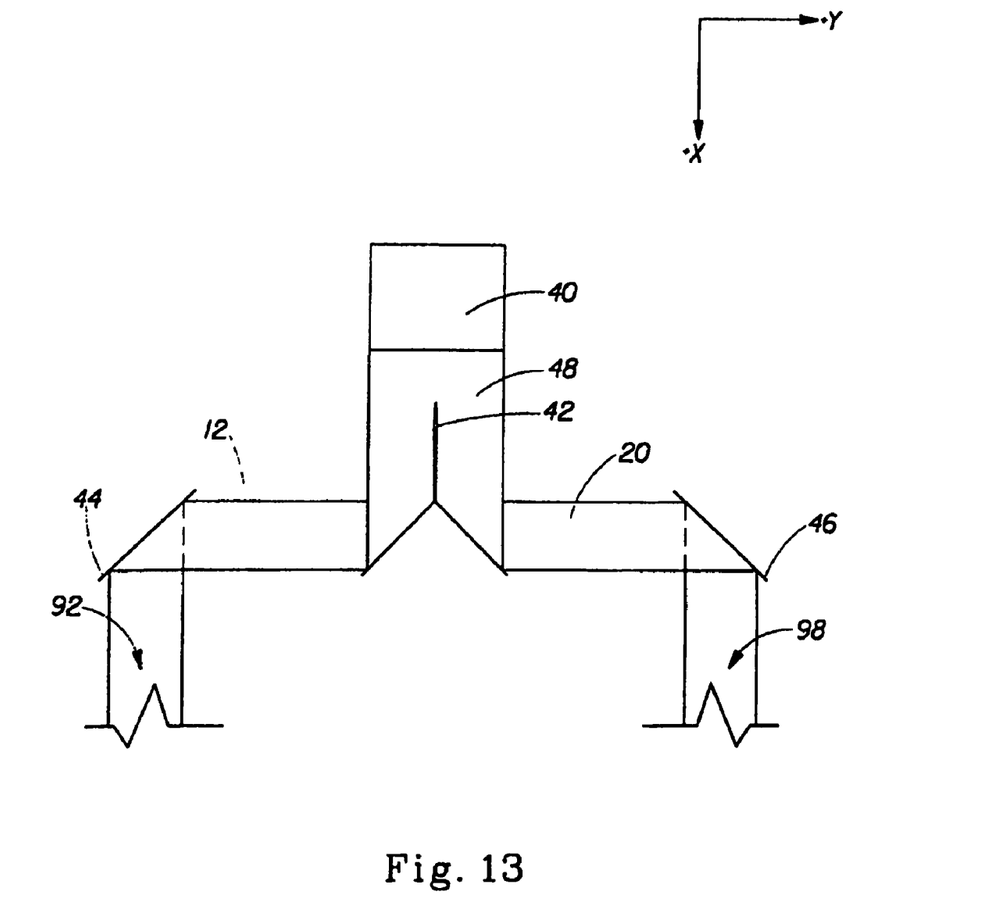
FIG. 13 is a plan view of an apparatus that implements an optional step in the claimed invention.

The first web 12 and second web 20 may be drawn from a single parent roll of material 40 which forms a parent web 48 and is cut via a slitter 42 as shown in FIG. 13. The slitter 42 may comprise any suitable device known in the art. For example, the slitter 42 can be a stationary blade or may comprise an anvil roll and a cutting roll. The anvil roll and cutting roll may be configured such that they create a scissor cut or create a crush cut in a parent web 48.

For this embodiment, the parent roll 40 unwinds and creates a parent web 48. The parent web 48 moves in the positive x direction towards the slitter 42. The slitter 42 cuts the parent web 48 and creates a first web 12 and a second web 20 from the parent web 48. The first web 12 and the second web 20 are then turned in a direction parallel to the y-axis, i.e. the first web 12 extends in the negative y direction while the second web 20 extends in the positive y direction. Then, the first web 12 and the second web 20 are turned such that the first web 12 and the second web 20 travel along a path parallel to the x-axis by the fifth turnbar 44 and the sixth turnbar 46, respectively. After going through the fifth turnbar 44, the first web 12 is provided to the first upstream zone 92. Similarly, after going through the sixth turnbar 46, the second web 20 is provided to the second upstream zone 98.

Figure 14:
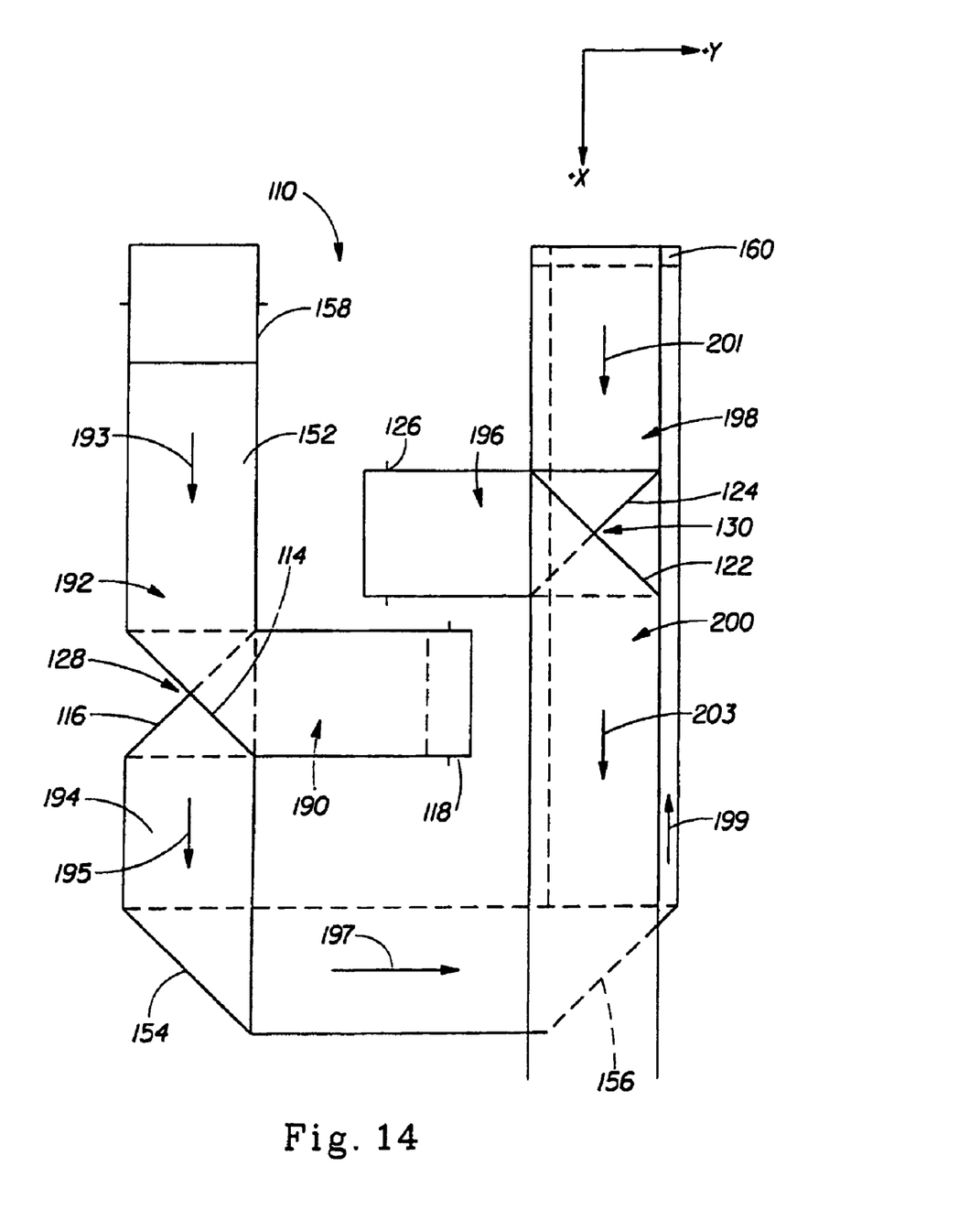
FIG. 14 is a plan view of an apparatus that can carry out a variation of the claimed invention.

Alternatively, the present invention may be performed on a single web 152 using the apparatus 110 an example of which is shown in FIG. 14. The single web 152 is fed from the unwind station 158 into the first upstream zone 192 at a first upstream zone velocity in the positive x direction 193. The single web 152 is diverted from the first upstream zone 192 into the first intermediate zone 190 and into the first assembly 128 by the first turnbar 114. The single web 152 is turned such that the single web 152 in the first intermediate zone 190 extends in the positive y direction parallel to the y-axis. The single web 152 is then inverted by the first idler 118 such that the single web 152 extends in the negative y direction. Then the single web 152 is diverted from the first intermediate zone 190 to the first downstream zone 194 by the second turnbar 116. The single web 152 is turned such that the single web 152 in the first downstream zone 194 moves in the positive x direction 195.

The single web 152 is transported to the second upstream zone 198 via the seventh turnbar 154, eighth turnbar 156, and third idler 160. The single web 152, from the first downstream zone 194 is diverted by the seventh Lumbar 154 such that the single web 152 moves in the positive y direction 197. The single web 152 is fed to the eighth turnbar 156 thereby turning the single web 152 such that the single web 152 moves in the negative x direction 199. The single web 152 is then inverted by the third idler 160 such that the single web 152 moves in the positive x direction 201 and into the second upstream zone 198 at a second upstream zone velocity.

The single web 152 is diverted from the second upstream zone 198 into the second intermediate zone 196 and into the second assembly 130 by the third turnbar 124. The single web 152 is turned such that the single web 152 in the second intermediate zone 196 extends in the negative y direction parallel to the y-axis. The single web 152 is then inverted by the second idler 126 such that the single web 152 extends in the positive y direction. Then the single web 152 is diverted from the second intermediate zone 196 to the second downstream zone 200 by the fourth turnbar 122. The single web 152 is turned such that the single web 152 in the second downstream zone 200 moves in the positive x direction 203.

The first assembly 128 and the second assembly 130 are periodically overlapped in an alternating fashion. Similar to the previous discussion, this allows a material to be continuously applied to the single web 152 in the first intermediate zone 190 and the second intermediate zone 196, respectively.

Also, the single web 152 can be combined with a third web or fourth web in a similar manner as described above with regard to FIG. 12. The combining in this instance could take place in the first downstream zone 194 or the second downstream zone 200 of the single web 152. Moreover, the step of separation may be accomplished in any manner described herein.

Figure 15:
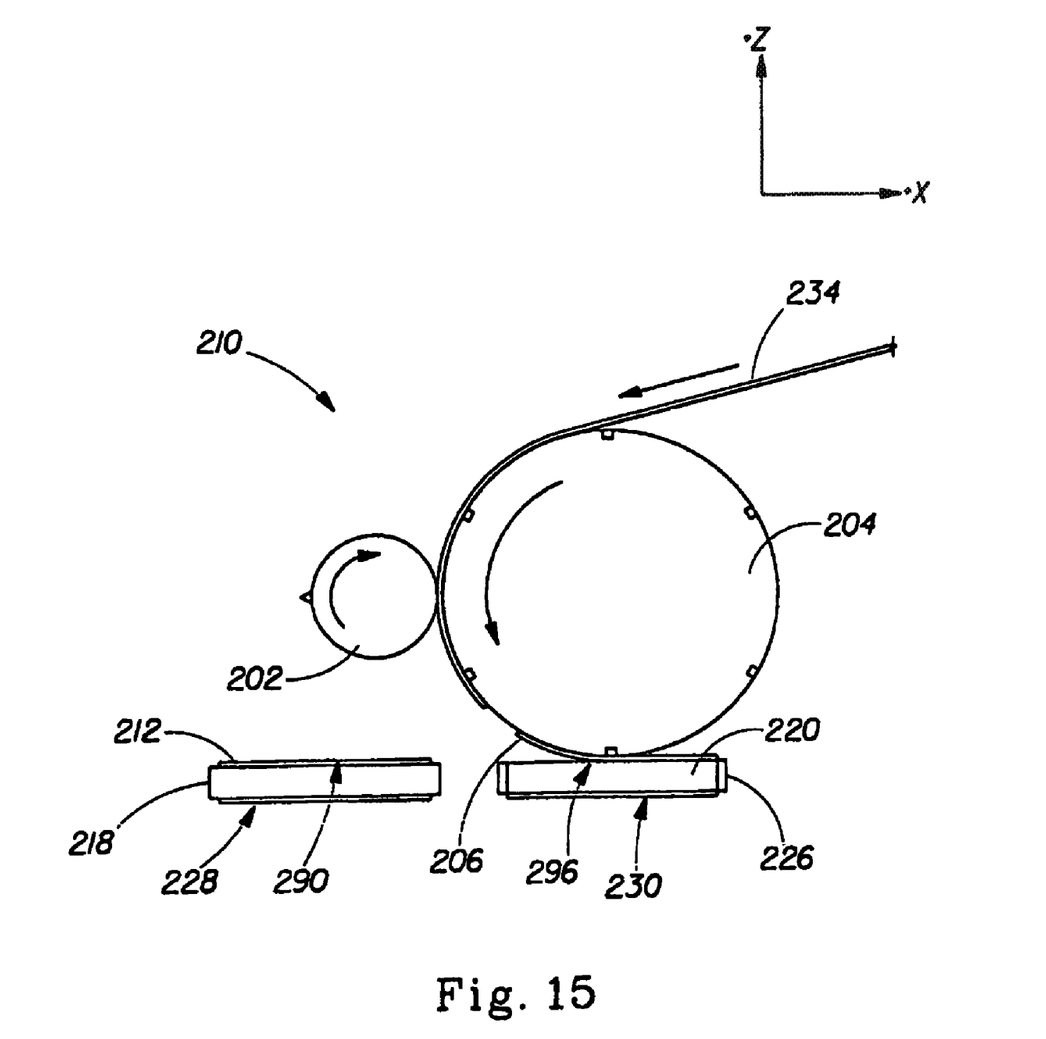
FIG. 15 is an elevation view of an apparatus that can carry out a variation of the claimed invention.

FIG. 15 shows an example of how discrete parts may be applied transversely to a moving web using apparatus 210. The separation occurs using an anvil roll 204 and a knife roll 202. The knife roll 202 has protrusions which engage the anvil roll 204 to create the discrete parts 206. Material 234 comprises a web and is partially looped around the anvil roll 204. As the protrusions of the knife roll 202 engage the anvil roll 204, discrete parts 206 are formed from the material 234. The anvil roll 204 engages the second web 220 in the second intermediate zone 296 in order to join the discrete part 206 to the second web 220 in the second intermediate zone 296. Thus, the discrete parts 206 are combined with the second web 220 in the second intermediate zone 296 as the second web 220 passes underneath the anvil roll 204.

After the second web 220 in the second intermediate zone 296 has received the discrete part, the second assembly 230 translates in the positive x direction such that the first assembly 228 can move into a position such that the first web 212 in the first intermediate zone 290 can receive the discrete part from the anvil roll 204. The anvil roll 204 has a tangential velocity which is equal to the velocity of the first assembly 228 when in contact with the first assembly 228. Similarly, the anvil roll 204 has a tangential velocity which is equal to the velocity of the second assembly 230 when in contact with the second assembly 230.

The motions of the first assembly 28 and the second assembly 30 discussed previously concerning FIGS. 2-5 are equally applicable in this instance regarding the first assembly 228 and the second assembly 230. Thus, the placement of discrete parts 206 on the first web 212 in the first intermediate zone 290 or the second web 220 in the second intermediate zone 296 may be implemented with any of the embodiments discussed herein.

Note that the turnbars mentioned herein, turn the first web second web or the single web in perpendicular directions. However, a turnbar may turn a web at any given angle provided that the first assembly and the second assembly are given enough distance between each other. Specifically, there must be enough distance between the longitudinal centerlines of each web allowing the first assembly and the second assembly to have sufficient space to turn their respective webs in the positive y direction and the negative y direction. Sufficient distance between the assemblies is required such that the first and second assemblies can periodically overlap one another thereby allowing their respective webs to receive the material 34 across their transverse width.

The devices described herein for diverting, turning, redirecting, or inverting a web have included turnbars and idlers. Despite this description, any suitable methods of diverting, turning or redirecting a web known in the art can be used in conjunction with the present invention. Also, any suitable methods of inverting a web known in the art may be used in conjunction with the present invention.

All embodiments mentioned within the specification are not constrained to the application of a material across the entire transverse width of the first web, second web, or single web. The material application may be across only a portion of the transverse width of the first web, second web, or single web. Also, the material application is not constrained to beginning at the leading edge of the first web, second web, or single web and is also not constrained to ending at the trailing edge of the first web, second web, or single web.

All documents cited in the Detailed Description of the Invention are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of placing a material on a single web having a transverse width, the method comprising the steps of:
   providing the single web in a first upstream zone such that the web is moving at a first upstream zone velocity in the positive x direction;
   providing a first means for diverting the single web from the first upstream zone to a first intermediate zone and for diverting the single web from the first intermediate zone to a first downstream zone;
   transporting the single web from the first downstream zone into a second upstream zone such that the single web is moving at a second upstream zone velocity in the positive x direction;
   providing a second means for diverting the single web from the second upstream zone to a second intermediate zone and for diverting the single web from the second intermediate zone to a second downstream zone;
   periodically overlapping the first means for diverting and the second means for diverting in an alternating fashion by translating the first means for diverting and the second means for diverting in a positive x direction in a first plane and a negative x direction in a second plane such that when the first means for diverting translates in the positive x direction, the single web in the first intermediate zone has a velocity, with respect to the first means for diverting, which is less than the first upstream zone velocity and such that when the second means for diverting translates in the positive x direction, the single web in the second intermediate zone has a velocity, with respect to the second means for diverting, which is less than the second upstream zone velocity; and
   alternately applying the material across at least a portion of the transverse width of the single web in the first intermediate zone and across at least a portion of the transverse width of the single web in the second intermediate zone such that the application of the material to the single web in the first intermediate zone and the single web in the second intermediate zone is continuous.

2. The method of claim 1 further comprising the step of combining the single web with a second web to create a laminate structure.

3. The method of claim 1, wherein the material comprises a continuously extruded polymer.

4. The method of claim 1, wherein the material comprises a continuously sprayed polymer.

5. The method of claim 1, wherein translating the first means for diverting in the positive x direction causes the single web in the first intermediate zone to be stationary with respect to the first means for diverting and wherein translating the second means for diverting in the positive x direction causes the single web in the second intermediate zone to be stationary with respect to the second means for diverting.

* * * * *